(12) United States Patent
Ikeda et al.

(10) Patent No.: US 6,212,417 B1
(45) Date of Patent: Apr. 3, 2001

(54) BIOSENSOR

(75) Inventors: Shin Ikeda, Katano; Toshihiko Yoshioka; Shiro Nankai, both of Hirakata, all of (JP)

(73) Assignee: Matsushita Electric Industrial Co., Ltd., Osaka-fu (JP)

( * ) Notice: Subject to any disclaimer, the term of this patent is extended or adjusted under 35 U.S.C. 154(b) by 0 days.

(21) Appl. No.: 09/379,128

(22) Filed: Aug. 20, 1999

(30) Foreign Application Priority Data

Aug. 26, 1998 (JP) .................................................. 10-239853

(51) Int. Cl.$^7$ ........................................................ A61B 5/05
(52) U.S. Cl. ............................. 600/345; 600/347; 204/403
(58) Field of Search ................................... 600/345, 346, 600/347, 365, 395, 396, 397; 204/403

(56) References Cited

U.S. PATENT DOCUMENTS

| | | | | |
|---|---|---|---|---|
| 4,224,125 | * | 9/1980 | Nakamura et al. | 204/403 |
| 4,897,173 | * | 1/1990 | Nankai et al. | 204/403 |
| 5,264,103 | * | 11/1993 | Yoshioka et al. | 204/403 |
| 5,496,453 | * | 3/1996 | Uenoyama et al. | 204/403 |
| 5,540,828 | * | 7/1996 | Yacynych | 204/418 |
| 5,575,895 | * | 11/1996 | Ikeda et al. | 204/403 |
| 5,582,697 | * | 12/1996 | Ikeda et al. | 204/403 |
| 5,695,947 | * | 12/1997 | Guo et al. | 435/11 |
| 5,906,921 | * | 5/1999 | Ikeda et al. | 435/25 |
| 5,922,188 | * | 7/1999 | Ikeda et al. | 204/403 |
| 5,985,116 | * | 11/1999 | Ikeda et al. | 204/403 |
| 6,059,946 | * | 5/2000 | Yukawa et al. | 204/403 |
| 6,104,940 | * | 8/2000 | Watanabe et al. | 600/345 |

FOREIGN PATENT DOCUMENTS

| | | |
|---|---|---|
| 02310457 | 12/1990 | (JP) . |
| 05340915 | 12/1993 | (JP) . |
| 06109693 | 4/1994 | (JP) . |
| 08320304 | 12/1996 | (JP) . |
| 09101280 | 4/1997 | (JP) . |

* cited by examiner

Primary Examiner—Cary O'Connor
Assistant Examiner—Navin Natnithithadha
(74) Attorney, Agent, or Firm—Akin, Gump, Strauss, Hauer & Feld, L.L.P.

(57) ABSTRACT

A highly reliable biosensor is provided which is reduced in influences of any interfering substance or preexisting oxygen in a sample solution. The biosensor comprises an electrode system including a working electrode, a counter electrode and a third electrode also usable as an interfering substance detecting electrode, a reagent layer containing at least an oxidoreductase and an electron mediator, and an electrically insulating base plate for supporting the electrode system and the reagent layer, wherein the third electrode is arranged at an opposing position to that of at least one of the working electrode and the counter electrode and the reagent layer is arranged at a predetermined position apart from the third electrode.

6 Claims, 3 Drawing Sheets

BIOSENSOR

BACKGROUND OF THE INVENTION

The present invention relates to a biosensor for rapid and simplified quantitation of a substrate in a sample with high accuracy.

Conventionally, methods using polarimetry, colorimetry, reductimetry, a variety of chromatography, etc. have been developed as the measure for quantitative analysis of sugars such as sucrose, glucose, etc. However, those conventional methods are all poorly specific to sugars and hence have poor accuracy. Among them, the polarimetry is simple in manipulation but is largely affected by the temperature at manipulation. Therefore, this method is not suitable for simple quantitation of sugar level at home by ordinary people.

On the other hand, a variety of biosensors have been developed recently which best utilize a specific catalytic action of enzymes.

In the following, a method of quantitative analysis of glucose will be described as an example of the method for quantitating a substrate in a sample solution. Conventionally known electrochemical quantitation of glucose is the method using a combination of glucose oxidase (EC 1.1.3.4; hereinafter abbreviated to "GOD") with an oxygen electrode or a hydrogen peroxide electrode (see "Biosensor" ed. by Shuichi Suzuki, Kodansha, for example).

GOD selectively oxidizes a substrate β-D-glucose to D-glucono-δ-lactone using oxygen as an electron mediator. Oxygen is reduced to hydrogen peroxide during the oxidation reaction by GOD in the presence of oxygen. A decreased volume of oxygen is measured by the oxygen electrode or an increased volume of hydrogen peroxide is measured by the hydrogen peroxide electrode. The decreased volume of oxygen or, otherwise, the increased volume of hydrogen peroxide is proportional to the content of glucose in the sample solution. Therefore, glucose concentration in the sample solution can be quantitated based on the decreased volume of oxygen or the increased volume of hydrogen peroxide.

However, as speculated from the oxidation reaction by GOD, this prior art method has a drawback of great influences on the measurement result of the oxygen concentration in the sample solution. In the event that oxygen is absent in the sample solution, this method does not allow measurement itself.

Under the circumstance, a glucose sensor of new type has been developed which uses as the electron mediator an organic compound or a metal complex such as potassium ferricyanide, a ferrocene derivative, a quinone derivative, etc., in place of oxygen in the sample solution. This sensor reoxidizes a reduced form electron mediator resulting from the enzyme reaction in order to determine the glucose concentration in the sample solution based on an oxidation current produced by the reoxidation reaction. The use of such organic compound or metal complex as the electron mediator in place of oxygen secures precise placement of a known amount of GOD together with the electron mediator in their stable state on an electrode system in forming a reagent layer on the electrode system. At that time, the reagent layer may be integrated with the electrode system while keeping the former in almost dry state. Therefore, a disposable glucose sensor based on this technology has recently been noted considerably. Such disposable glucose sensor facilitates measurement of glucose concentration using a measurement device exclusive to the sensor by simple introduction of a sample solution into the sensor detachably connected to the measurement device. The application of this technique is not limited to glucose quantitation and may be extended to quantitation of any other substrate present in the sample solution.

Measurement using the above-mentioned sensor determines substrate concentration in a sample based on an oxidation current that flows upon oxidation of a reduced form electron mediator on a working electrode. However, when the sample is blood, fruit juice or something like that, any easy-to-be-oxidized substance, such as ascorbic acid, uric acid, etc., in the sample will be oxidized on the working electrode together with the reduced form electron mediator. This oxidation of easy-to-be-oxidized substance sometimes produces an adverse effect on the measurement result.

The measurement using the above-mentioned sensor has another problem of simultaneous developments of reduction of the electron mediator carried on the reagent layer with generation of hydrogen peroxide by using dissolved oxygen in the sample as an electron mediator. Furthermore, the hydrogen peroxide thus generated acts to reoxidize the reduced form electron mediator. This sometimes results in production of negative errors in the results of measurement by the dissolved oxygen when the substrate concentration is to be determined based on the oxidation current of the reduced form electron mediator.

BRIEF SUMMARY OF THE INVENTION

In order to solve the above-mentioned problem of the prior art biosensors, the object of the present invention is to provide a biosensor comprising an electrically insulating base plate, an electrode system including a working electrode, a counter electrode and a third electrode which can also serve as an interfering substance detecting electrode, and a reagent layer containing at least an oxidoreductase and an electron mediator, wherein the third electrode is arranged at an opposing position to that of at least one of the working electrode and the counter electrode or the both, and the reagent layer is arranged at a predetermined position somewhere apart from the third electrode.

The normal positional relationship between the reagent layer and the third electrode is such that the reaction layer is located downstream from the third electrode inside the sample solution supply pathway.

The reaction layer is preferably formed in contact with the opposing electrode to the third electrode, the working electrode and/or the counter electrode. However, it is not always necessary to form the reagent layer downstream from the third electrode if the sample solution which has been introduced into the sensor but has not yet dissolved the reagent layer, in other words, which is free of reduced form electron mediator contains anything oxidizable by the third electrode and an oxidation current for oxidizing such oxidizable substance can be measured before the sample solution dissolving the reagent layer and hence containing reduced electron mediator by the enzyme reaction arrives at the third electrode.

It is preferred to form a layer essentially containing lecithin at a predetermined position somewhere apart from the third electrode, preferably at a position in contact with the reagent layer.

Preferably, the reagent layer further contains a hydrophilic polymer.

While the novel features of the invention are set forth particularly in the appended claims, the invention, both as to organization and content, will be better understood and appreciated, along with other objects and features thereof, from the following detailed description taken in conjunction with the drawings.

DETAILED DESCRIPTION OF THE INVENTION

Figure 1:
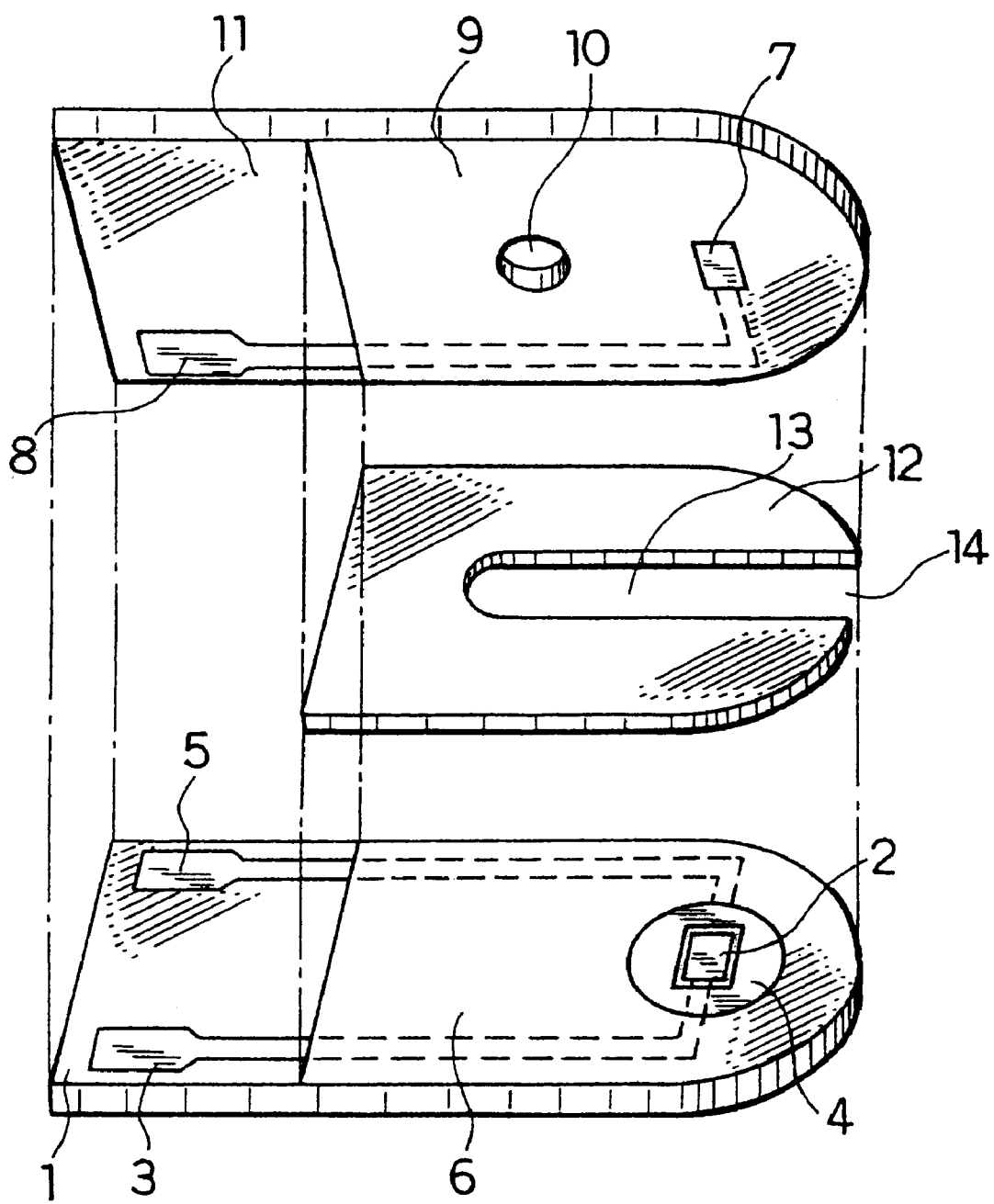
FIG. 1 is an exploded perspective view illustrating a glucose sensor of one example in accordance with the present invention, from which the reagent layer has been omitted.

The biosensor in accordance with the present invention is a modification of a prior art biosensor comprising an electrode system including a working electrode and a counter electrode, a reagent layer containing an oxidoreductase and an electron mediator, and an electrically insulating base plate for supporting the electrode system and the reagent layer, wherein a sample solution is supplied to the reagent layer to cause an enzyme reaction to reduce the electron mediator and the resultant reduced form electron mediator is reoxidized on the working electrode to determine the substrate concentration in the sample solution from an oxidation current flowing during reoxidation reaction. More specifically, the present invention adds, to the above-mentioned biosensor, an additional third electrode doubling as an interfering substance detecting electrode which is arranged at an opposing position to that of at least one of the working electrode and the counter electrode, and arranges the reagent layer at a predetermined position apart from the third electrode.

In a preferred mode of the present invention, the biosensor comprises an electrically insulating base plate, an electrically insulating cover member for forming a sample solution supply pathway between the cover member and the base plate, and an electrode system and a reagent layer, both being formed on the base plate or the cover member so as to be exposed to the sample solution supply pathway, wherein the third electrode is arranged at an opposing position to that of at least one of the working electrode and the counter electrode and the reagent layer is arranged at a position somewhere apart from the third electrode inside the sample solution supply pathway.

In a further preferred mode of the present invention, the cover member is composed of an electrically insulating base plate and a spacer having a slit for forming the sample solution supply pathway. More specifically, the biosensor is composed of two sheets of electrically insulating base plate and a spacer. In a first concrete example of the above-mentioned structure of the biosensor in accordance with the present invention, the working and the counter electrodes are formed on one of the base plates and the third electrode on the other. In a second concrete example of the structure, only the working electrode is formed on one of the base plates and the counter and the third electrodes on the other. In a third concrete example, the working and the third electrodes are formed on one of the base plates and the counter electrode on the other. In the first and the second examples, the reagent layer is formed on the base plate having the working electrode thereon. In the third example, it is formed on the base plate having the counter electrode.

It is desirable to form the reagent layer at a position in contact with the electrode which is opposed to the third electrode. However, the present invention is not limited to this arrangement and the reagent layer may be arranged at an alternative position such that a raw sample solution can arrive at the third electrode some time before the arrival at the third electrode of a product of the enzyme reaction due to dissolution of the reagent layer in the sample solution supplied on the path of the sample solution supply pathway.

According to the structure of the biosensor in accordance with the present invention, if the sample solution contains an easy-to-be-oxidized substance, the oxidation current that flows across the third and the counter electrodes at an initial stage of measurement after sample supply, in other words, before arrival of the reduced form electron mediator as a product of enzyme reaction at the third electrode reflects only the concentration of the easy-to-be-oxidized substance. The subsequent measurement of the oxidation current across the working and the counter electrodes after a lapse of enough time reflects the current produced by the oxidation reaction of the easy-to-be-oxidized substance in the sample solution and the oxidation reaction of the reduced form electron mediator resulting from the enzyme reaction. Therefore, a correction of the oxidation current value obtained by the subsequent measurement by that obtained by the initial measurement gives a precise concentration of the substrate in the sample.

If the sample as supplied contains oxygen, application of an appropriate potential onto the third electrode at an initial stage of measurement after sample supply as mentioned above enables measurement of the oxidation current reflecting the concentration of the dissolved oxygen in the sample. When the substrate concentration in the sample is determined from an oxidation current required for reoxidizing the reduced form electron mediator due to enzyme reaction, the dissolved oxygen in the sample produces negative errors in the measured values. However, a similar correction for the measured value by the oxidation current reflecting the dissolved oxygen can give a precise substrate concentration from which any influence of the dissolved oxygen has been excluded.

In the present invention, the oxidoreductase to be contained in the reagent layer is selected to fit for the type of substrate in the sample solution. Exemplary oxidoreductases include fructose dehydrogenase, glucose oxidase, alcohol oxidase, lactate oxidase, cholesterol oxidase, xanthine oxidase, amino acid oxidase, etc.

Examples of electron mediator include potassium ferricyanide, p-benzoquinone, phenazine methosulfate, methylene blue, ferrocene derivatives. These electron mediators are used singly or in combinations of two or more.

The above-mentioned enzyme and electron mediator may be dissolved in the sample solution. Otherwise, they may be prevented form being dissolved in the sample solution by fixing the reagent layer to the base plate or others. If the latter is adopted, it is preferable for the reagent layer to further contain one of the below-mentioned hydrophilic polymers.

A variety of hydrophilic polymers are applicable to the reagent layer. Exemplary hydrophilic polymers for that purpose include carboxymethyl cellulose, hydroxyethyl cellulose, hydroxypropyl cellulose, methyl cellulose, ethyl cellulose, ethylhydroxyethyl cellulose, carboxymethylethyl cellulose, polyvinyl pyrrolidone, polyvinyl alcohol, polyamino acid such as polylysine, polystyrene sulfonate, gelatin and its derivatives, a polymer of acrylic acid or an acrylate, a polymer of methacrylic acid or a methacrylate, starch and its derivatives, a polymer of maleic anhydride or a maleate, etc. Of them, carboxymethyl cellulose, hydroxyethyl cellulose, hydroxypropyl cellulose, methyl cellulose, ethyl cellulose, ethylhydroxyethyl cellulose, and carboxymethylethyl cellulose are preferred.

In the below-mentioned examples, although a potential of 500 mV or −1,300 mV is applied onto the third electrode in order to sense supply of the sample solution and to detect existing ascorbic acid or oxygen in the sample solution, the present invention is not limited to those potential values. Similarly, although a potential of 500 mV is applied onto the working electrode in order to obtain a response current, the present invention is not limited to this value and any potential value at which the reduced form electron mediator as a product of a series of reaction can be reoxidized may be used. Furthermore, the timing of measurement of the current value is not limited to the specific ones given in the below-mentioned examples.

In the below-mentioned examples, some examples of the electrode system are shown. However, the present invention is not limited to those examples with respect to the shape of electrode, arrangement of the electrodes and their leads, and method of combination with other sensor members.

In the below-mentioned examples, although carbon is used as the material of the third electrode, the present invention is not limited to carbon and any other conductive material as well as silver/silver chloride electrode may be used similarly.

In the following, the present invention will be described more specifically by means of concrete examples.

EXAMPLE 1

A glucose sensor will be described herein as an example of biosensor. FIG. 1 is an exploded perspective view illustrating the glucose sensor of Example 1 with an omission of the reagent layer.

A working electrode 2 and a counter electrode 4 are formed on an electrically insulating base plate 1, together with lead terminals 3 and 5 which are electrically connected to the working and the counter electrodes 2 and 4, respectively. A third electrode 7 is formed on another electrically insulating base plate 11 together with a lead terminal 8 which is electrically connected to the third electrode 7. A circular reagent layer (not shown) is formed on the base plate 1 such that the periphery of the reagent layer comes along the periphery of the counter electrode 4 so as to cover both the working electrode 2 and the counter electrode 4. Numerals 6 and 9 in the figure represent insulating layers.

The glucose sensor of Example 1 is assembled using two sheets of electrically insulating base plate 1 and 11 made of polyethylene terephthalate and a spacer 12 which is to be sandwiched between the two base plates 1 and 11. These members are adhered to each other in a positional relationship as shown by a dashed line in FIG. 1 which yields a glucose sensor.

The spacer 12 is provided with a slit 13 for forming a sample solution supply pathway. The electrically insulating base plate 11 is provided with an air vent 10. The base plates 1 and 11 are laminated and adhered to each other with the spacer 12 being placed therebetween. As a result, a space (not shown) which functions as the sample solution supply pathway can be formed by the base plates 1, 11 and the spacer 12. An open end 14 of the slit which is a starting side of the space functions as a sample solution supply port and a terminal side of the space communicates with the air vent 10.

A combination of the base plate 11 and the spacer 12 corresponds to the cover member as mentioned before. The cover member of this biosensor is composed of two members. However, it may be formed with only one member having a groove corresponding to the slit 13 of the spacer 12.

The glucose sensor of Example 1 was produced as follows.

A silver paste was printed on the electrically insulating base plate 1 made of polyethylene terephthalate using a known screen printing method to form the lead terminals 3 and 5. An identical silver paste was printed on the other electrically insulating base plate 11 in the same manner to form the lead terminal 8. Then, a conductive carbon paste containing a resin binder is printed on the base plate 1 to form thereon the working electrode 2. The third electrode 7 was formed on the other base plate 11 in the same manner. The working electrode 2 and the third electrode 7 were electrically connected to the lead terminals 3 and 8, respectively.

Next, an insulating paste was printed on the two base plates 1 and 11 to form an insulating layer 6 on the base plate 1 and an insulating layer 9 on the base plate 11.

The insulating layer 6 covers the periphery of the working electrode 2 and the insulating layer 9 the periphery of the third electrode 7, whereby the exposed area of each of the working electrode 2 and the third electrode 7 can be kept constant. The insulating layers 6 and 9 also cover the lead terminals 3, 5 and partially the lead terminal 8.

Then, an identical conductive carbon paste containing a resin binder was printed on the base plate 1 to form thereon the counter electrode 4. The counter electrode 4 was electrically connected to the lead terminal 5.

Next, an aqueous solution containing GOD as the oxidoreductase and potassium ferricyanide as the electron mediator was dropped on the working electrode 2 and the counter electrode 4 and dried to form the reagent layer.

Then, in order to enhance smooth supply of the sample solution to the reagent layer more, a lecithin layer was formed on the reagent layer by spreading an organic solvent solution of lecithin, for example, a toluene solution of lecithin from the sample solution supply port 14 toward the reagent layer and drying it.

At that time, arrangement of the lecithin layer at a position in contact with the third electrode 7 will increase variations in the sensor response. This may be due to development of a change on the surface of the third electrode by the presence of the lecithin layer.

Finally, the base plates 1 and 11 and the spacer 12 were adhered to each other in a positional relationship as shown by the dashed line in FIG. 1 which gave the glucose sensor of Example 1.

At production, if the third electrode 7, the working electrode 2 and the counter electrode 4 are arranged on the same plane, the reagent layer covers the third electrode 7 partially, yielding an error in the results of measurement. However, in the sensor as exemplified above, the third electrode 7 is arranged at an opposing position to the working electrode 2 and the counter electrode 4. This arrangement of the third electrode drastically reduces errors in the measurement results induced by the lecithin layer as noted above.

The glucose sensor thus produced was placed in a measurement device exclusive to the sensor. Then, a potential of 500 mV was applied onto the third electrode 7 using the counter electrode 4 as reference. While applying the potential, 3 µl of an aqueous glucose solution containing ascorbic acid as an interfering substance was supplied to the sensor as a sample through the sample solution supply port 14. The sample solution advanced to the air vent 10 through the space and dissolved the reagent layer on the electrode system.

Upon supply of the sample solution, the system detecting supply of the sample was actuated based on an electrical change between the third electrode 7 and the counter electrode 4, that is, based on the liquid junction between the above two electrodes due to the sample solution and the timer equipped in the measurement device started to operate. At that time, while the potential was kept applied across the third electrode 7 and the counter electrode 4, the current flowing across the two electrodes was measured after a lapse of certain time from the detection of supply of the sample solution. The obtained current value which was derived from the oxidation reaction of the ascorbic acid contained in the sample solution as an interfering substance was proportional to the concentration of the ascorbic acid. After measurement of the current value across the third and the counter electrodes 7 and 4, the application of potential to the two electrodes was stopped.

As noted above, the third electrode 7 is formed at an opposing position to the working electrode 2 and the counter electrode 4 and located apart from the reagent layer. Therefore, it will take some time until arrival at the third electrode 7 of the ferrocyanide ion as a product of enzyme reaction on the reagent layer. In other words, the current value across the third and the counter electrodes 7 and 4 until arrival of ferrocyanide ion at the third electrode can reflect the concentration of only ascorbic acid.

Then, a potential of 500 mV was applied onto the working electrode 2 using the counter electrode 4 as reference 25 seconds after detection of supply of the sample solution and the current value across the working and the counter electrodes 2 and 4 was measured after 5 seconds.

When the reagent layer is dissolved in the sample solution, reaction of glucose, GOD and ferricyanide ion develops in the resultant mixed solution to cause oxidation of glucose to gluconolactone and reduction of ferricyanide ion to ferrocyanide ion. The concentration of ferrocyanide ion is proportional to the concentration of glucose. The current across the working and the counter electrodes 2 and 4 30 seconds after detection of supply of the sample solution is due to the oxidation reaction between the ferrocyanide ion and the preexisting ascorbic acid. This means that the preexisting ascorbic acid produces a positive error in the result of measurement. However, as mentioned before, the current across the third and the counter electrodes 7 and 4 reflects the concentration of only ascorbic acid. Therefore, a correction of the subsequent measurement value on the basis of the oxidation current of ascorbic acid gives a precise concentration of glucose from which any influence of ascorbic acid has been excluded.

EXAMPLE 2

A glucose sensor was produced in the same manner as in Example 1 except for further inclusion of carboxymethyl cellulose (hereinafter abbreviated to "CMC") in the reagent layer. Then, the sensor was tested in the same manner as in Example 1.

First, an aqueous CMC solution was dropped on the working electrode 2 and the counter electrode 4 on the base plate 1 and dried to form a CMC layer. Then, a mixed aqueous solution of the enzyme and the electron mediator was dropped on the CMC layer. This caused temporary dissolution of the CMC layer and the subsequent drying of the layer yielded a reagent layer in which the enzyme, electron mediator and CMC have been mixed. However, when the CMC layer dissolved, since the mixed aqueous solution dissolving the CMC layer was not stirred, the enzyme, electron mediator and CMC were not mixed completely. As a result, the surface of the electrode system was coated with only CMC. More specifically, since the surface of the electrode system was protected from contact with the enzyme and the electron mediator, adsorption of protein onto the surface of the electrode system could be prevented.

This structure decreased variations in the sensor response.

EXAMPLE 3

Figure 2:
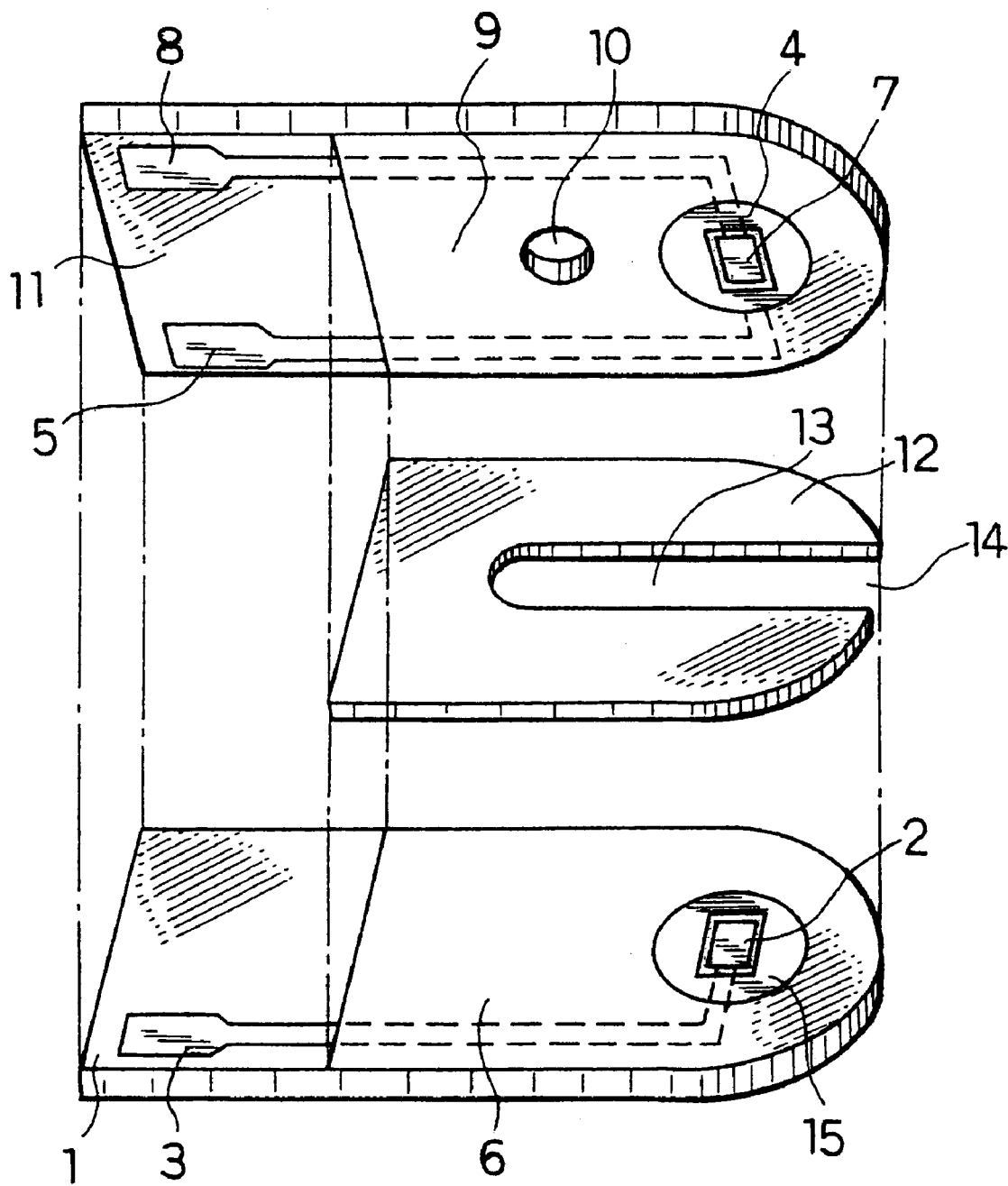
FIG. 2 is an exploded perspective view illustrating a glucose sensor of another example in accordance with the present invention, from which the reagent layer has been omitted.

FIG. 2 is an exploded perspective view of the glucose sensor of Example 3 with an omission of the reagent layer.

The working electrode 2 was formed on the electrically insulating base plate 1 together with a carbon layer 15, and the third electrode 7 and the counter electrode 4 were formed on the other electrically insulating plate 11 following the method used in Example 1. Then, the reagent layer and the lecithin layer were formed on the working electrode 2 and the carbon layer 15 following the method used in Example 2. In this structure, although the carbon layer 15 did not function as an electrode, arrangement of the carbon layer 15 around the working electrode 2 facilitated formation of the reagent layer. Adhesion of the base plates 1 and 11 with the spacer 12 being placed therebetween as was done in Example 1 yielded the glucose sensor of Example 3.

Then, similar to Example 1, an aqueous solution of glucose mixed with ascorbic acid was used to measure the glucose concentration by the glucose sensor. The result showed a precise glucose concentration from which the influence of ascorbic acid has been excluded.

When the range of glucose concentration is high (about 1,000 mg/dl or more), the current flowing across the working and the counter electrodes 2 and 4 increases. More specifically, the high glucose concentration produces a great increase in the amount of byproduct on the counter electrode 4. Therefore, arrangement of the counter electrode around the working electrode may sometimes allow the byproduct to exert adverse influences on the sensor response. However, the arrangement of the working and the counter electrodes as used in the present example best prevents such adverse influences.

EXAMPLE 4

Figure 3:
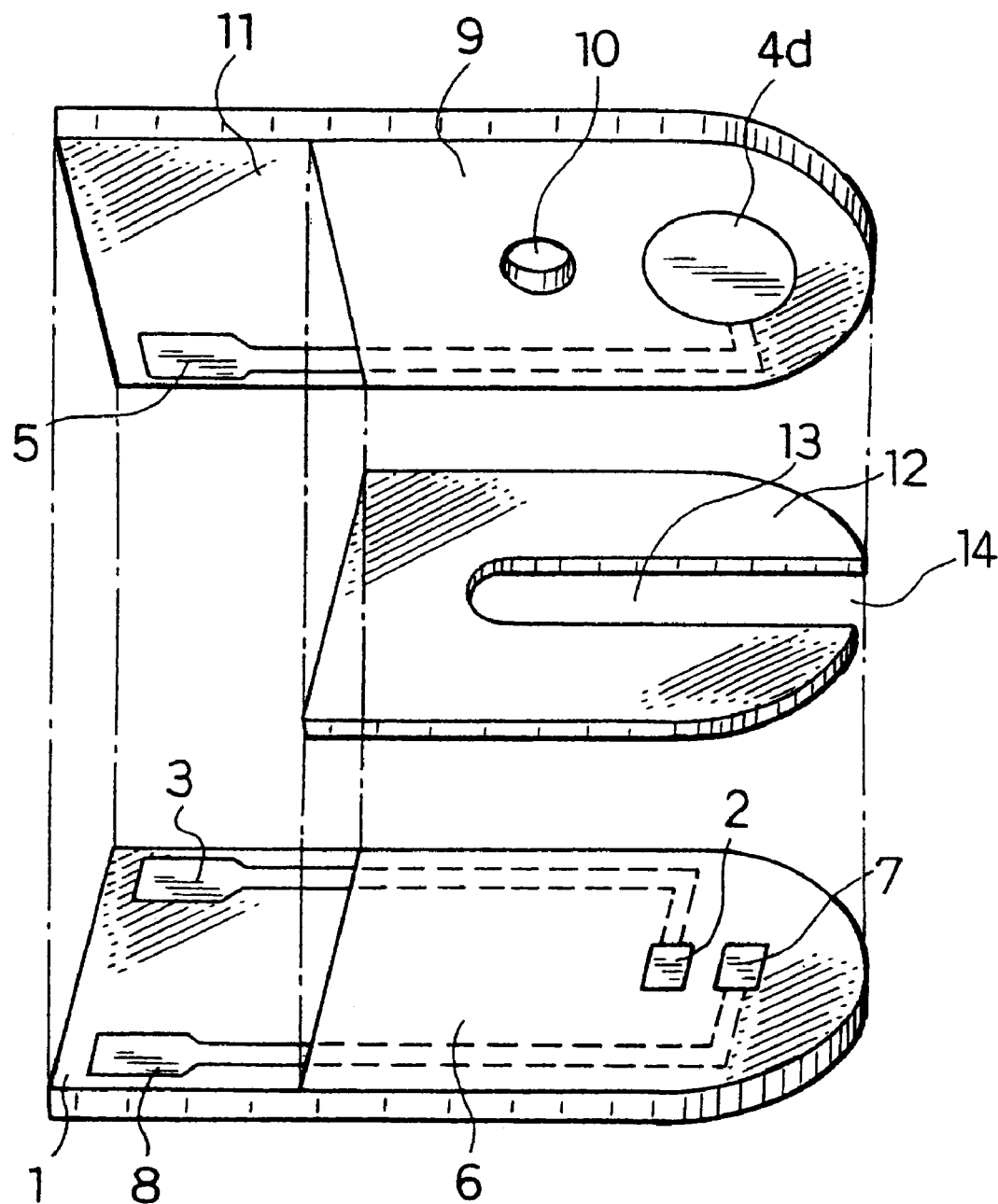
FIG. 3 is an exploded perspective view illustrating a glucose sensor of still another example in accordance with the present invention, from which the reagent layer has been omitted.

FIG. 3 is an exploded perspective view of the glucose sensor of Example 4 with an omission of the reagent layer.

The working electrode 2 and the third electrode 7 were formed on the electrically insulating base plate 1, and a counter electrode 4*d* on the other electrically insulating plate 11 following the method used in Example 1. Then, the reagent layer and the lecithin layer were formed on the counter electrode 4*d* following the method used in Example 2. Finally, similar to Example 1, the base plates 1 and 11 were adhered to each other with the spacer 12 being placed therebetween to complete the glucose sensor of Example 4.

Then, similar to Example 1, an aqueous solution of glucose mixed with ascorbic acid was used to measure the glucose concentration by the glucose sensor. The result showed a precise glucose concentration from which the influence of ascorbic acid has been excluded.

The effects of this example are: a larger area can be retained for the counter electrode 4d than for the working and the third electrodes 2 and 7, and the reference potential, which is used at application of a potential, can be stabilized more due to the positioning of the reagent layer on the counter electrode 4d.

The above effects decreased variations in the sensor response.

EXAMPLE 5

A glucose sensor was produced in the same manner as in Example 2.

The glucose sensor thus produced was placed in a measurement device exclusive to the sensor. Then, a potential of −1,300 mV was applied onto the third electrode 7 using the counter electrode 4 as reference. While applying the potential, 3 μl of an air-saturated aqueous glucose solution was supplied to the sensor as a sample through the sample solution supply port 14. The sample solution advanced to the air vent 10 through the space and dissolved the reagent layer on the electrode system.

Upon supply of the sample solution, the system detecting supply of the sample solution was actuated based on an electrical change between the counter electrode 4 and the third electrode 7 and the timer equipped in the measurement device started to operate. At that time, while the potential was kept applied across the counter electrode 4 and the third electrode 7, the current flowing across the two electrodes was measured after a lapse of certain time from the detection of supply of the sample solution.

The obtained current value is normally derived from the reduction reaction of the dissolved oxygen in the sample solution; however, supply of a glucose solution deaired with argon resulted in a drastic decrease in the reduction current.

After the current across the counter electrode 4 and the third electrode 7 was measured, the application of potential across the two electrodes was stopped.

As noted before, the reagent layer was omitted from the third electrode 7. Therefore, it will take some time until arrival close to the third electrode of the ferricyanide ion contained in the reagent layer. In other words, the current value across the counter and the third electrodes 4 and 7 before the arrival of ferricyanide ion close to the third electrode can reflect the concentration of only the dissolved oxygen.

Then, a potential of 500 mV was applied onto the working electrode 2 using the third electrode 7 as reference 25 seconds after detection of supply of the sample solution and the current value across the counter and the working electrodes 4 and 2 was measured after 5 seconds.

When the reagent layer is dissolved in the sample solution, reaction of glucose, GOD and ferricyanide ion develops in the resultant mixed solution to cause oxidation of glucose to gluconolactone and reduction of ferricyanide ion to ferrocyanide ion. At that time, enzyme reaction proceeds as a competitive reaction to the above oxidation and reduction so as to produce gluconolactone and hydrogen peroxide using the dissolved oxygen as an electron mediator. The hydrogen peroxide generated by the enzyme reaction acts to reoxidize ferrocyanide ion to ferricyanide ion. The dissolved oxygen, therefore, produces a negative error in the result of measurement if the glucose concentration is derived from the oxidation current required for oxidizing ferrocyanide ion.

However, as explained above, the current across the counter electrode 4 and the third electrode 7 reflects the concentration of only the dissolved oxygen. Therefore, a correction of the measurement result with the oxygen concentration yields a precise glucose concentration from which the influence of the dissolved oxygen has been excluded.

EXAMPLE 6

A glucose sensor was produced in the same manner as in Example 2.

The glucose sensor thus produced was placed in a measurement device exclusive to the sensor. Then, a potential of 500 mV was applied onto the third electrode 7 using the counter electrode 4 as reference. While applying the potential, 3 μl of an air-saturated aqueous glucose solution containing ascorbic acid was supplied to the sensor as a sample through the sample solution supply port 14. The sample solution advanced to the air vent 10 through the space and dissolved the reagent layer on the electrode system.

Upon supply of the sample solution, the system detecting supply of the sample solution was actuated based on an electrical change between the counter electrode 4 and the third electrode 7 of the electrode system and the timer equipped in the measurement device started to operate. At that time, the potential was kept applied across the counter electrode 4 and the third electrode 7.

Two seconds after detection of supply of the sample solution, the potential to be applied onto the third electrode 7 was changed to −1,300 mV. The current across the counter and the third electrodes 4 and 7 was measured at two points immediately before and 3 seconds after changing the potential value to −1,300 mV.

The current immediately before the potential change is dependent mainly on the concentration of ascorbic acid. On the other hand, the current 3 seconds after the potential change is dependent mainly on the dissolved oxygen.

After measurement of the current across the two electrodes 2 seconds and 5 seconds after supply of the sample solution, the application of potential was stopped.

Then, 25 seconds after detection of supply of the sample solution, a potential of 500 mV was applied onto the working electrode 2 using the third electrode 7 as reference, and the current flowing between the counter electrode 4 and the working electrode 2 was measured after 5 seconds.

As noted above, the current across the counter and the third electrodes 4 and 7 reflects the concentration of the existing ascorbic acid and oxygen. Therefore, their concentration can be determined from this current value. A correction of the result of measurement by the concentration of the ascorbic acid and oxygen yields a precise glucose concentration from which the influence of these substances has been excluded.

As discussed above, the present invention can provide a highly reliable biosensor which can eliminate adverse influences of any substance other than the substrate in a sample.

Although the present invention has been described in terms of the presently preferred embodiments, it is to be understood that such disclosure is not to be interpreted as limiting. Various alterations and modifications will no doubt become apparent to those skilled in the art to which the present invention pertains, after having read the above disclosure. Accordingly, it is intended that the appended claims be interpreted as covering all alterations and modifications as fall within the true spirit and scope of the invention.

What is claimed is:

1. A biosensor comprising:

an electrode system including a working electrode, a counter electrode and a third electrode which serves as an interfering substance detecting electrode, a reagent layer containing at least an oxidoreductase and an electron mediator, and an electrically insulating base plate for supporting said electrode system and said reagent layer, wherein said third electrode is arranged at an opposing position to that of at least one of the working electrode and the counter electrode and said reagent layer is arranged at a predetermined position apart from the third electrode.

2. A biosensor comprising:

an electrically insulating base plate, an electrically insulating cover member for forming a sample solution supply pathway between the cover member and said base plate, an electrode system including a working electrode, a counter electrode and a third electrode which serves as an interfering substance detecting electrode, and a reagent layer wherein said electrode system and said reagent layer are formed on said base plate or said cover member so as to be exposed to said sample solution supply pathway, and said third electrode is arranged at an opposing position to that of at least one of the working electrode and the counter electrode and said reagent layer is arranged at a position somewhere apart from the third electrode.

3. The biosensor in accordance with claim 1, wherein a layer essentially containing lecithin is arranged at a predetermined position avoiding said third electrode.

4. The biosensor in accordance with claim 2, wherein a layer essentially containing lecithin is arranged at a predetermined position avoiding said third electrode.

5. The biosensor in accordance with claim 1, wherein said reagent layer further contains a hydrophilic polymer.

6. The biosensor in accordance with claim 2, wherein said reagent layer further contains a hydrophilic polymer.

* * * * *